United States Patent [19]
Goodwin et al.

[11] Patent Number: 6,049,380
[45] Date of Patent: Apr. 11, 2000

[54] SINGLE MOLECULE IDENTIFICATION USING SELECTED FLUORESCENCE CHARACTERISTICS

[75] Inventors: Peter M. Goodwin; James H. Jett; Richard A. Keller; Alan K. Van Orden, all of Los Alamos, N.Mex.; Nicholas P. Machara, Germantown, Md.

[73] Assignee: Regents of the University of California, Los Alamos, Mexico

[21] Appl. No.: 09/169,025

[22] Filed: Oct. 9, 1998

Related U.S. Application Data

[60] Provisional application No. 60/065,365, Nov. 12, 1997.

[51] Int. Cl.⁷ .............................. G01N 21/64; G01J 3/30; F21V 9/16
[52] U.S. Cl. ........................ 356/317; 356/237; 250/458.1
[58] Field of Search ..................................... 356/317, 318, 356/72, 73, 417; 250/458.1, 459.1, 461.1, 461.2; G01N 21/64

[56] References Cited

U.S. PATENT DOCUMENTS

| | | | |
|---|---|---|---|
| 4,979,824 | 12/1990 | Mathies et al. | 356/318 |
| 5,208,651 | 5/1993 | Buican | 356/346 |
| 5,209,834 | 5/1993 | Shera | 204/183 |

OTHER PUBLICATIONS

Steven A. Soper, Lloyd M. Davis, and E. Brooks Shera, "Detection and Identification of Single Molecules in Solution," J. Opt. Soc. Am. B, vol. 9, No. 10, pp. 1761–1769, Oct. 1992.

Peter M. Goodwin, Charles W. Wilkerson, Jr., W. Patrick Ambrose, and Richard A. Keller, "Ultrasensitive Detection of Single Molecules in Flowing Sample Streams by Laser–Induced Fluorescence." SPIE, vol. 1895, Ultrasensitive Laboratory Diagnostics, pp. 79–89, 1993.

Joel Tellinghulsen, W. Patrick Ambrose, John C. Martin, and Richard A. Keller, "Analysis of Fluorescence Lifetime Data for Single Rhodamine Molecules in Flowing Sample Streams," Anal. Chem., vol. 66, pp. 64–72, 1994.

M. Sauer, K. T. Han, R. Muller, S. Nord, A Schulz, S. Seeger, J. Wolfrum, J. Arden–Jacob, G. Deltau, N. J. Marx, C. Zander, and K. H. Drexhage, "New Fluorescent Dyes in the Red Region for Biodiagnostics," Journal of Fluorescence, vol. 5, No. 3, pp. 247–261, 1995.

P. M. Goodwin, R. L. Affleck, W. P. Ambrose, J. N. Demas, J. H. Jett, J. C. Martin, L. J. Reha–Krantz, D. J. Semin, J. A. Schecker, M. Wu, and R. A. Keller, "Progress Toward DNA Sequencing at the Single Molecule Level," Experimental Technique of Physics, vol. 41, No. 2, pp. 279–294, 1995.

(List continued on next page.)

*Primary Examiner*—Frank G. Font
*Assistant Examiner*—Layla Lauchman
*Attorney, Agent, or Firm*—Ray G. Wilson

[57] ABSTRACT

Single fluorescent molecules in a flowing sample stream are distinguished and identified using only a single laser excitation wavelength. A sample stream is formed containing a dilute mixture of single molecule fluorophores, wherein each one of the fluorophores is serially ordered in the sample stream. The sample stream is illuminated with s single excitation wavelength laser effective to excite each fluorophore one at a time. Fluorescence emission photons from each said fluorophore are detected. A burst size is determined for each fluorophore to identify each fluorophore. A pulsed laser may be used, where burst size and an intra-burst fluorescence decay rate for each fluorophore are determined simultaneously from the detected fluorescence emission photons. The burst size and the decay rate are correlated to identify each fluorophore.

18 Claims, 6 Drawing Sheets

OTHER PUBLICATIONS

Li–Qiang Li and Lloyd M. Davis, "Rapid and Efficient Detection of Single Chromophore Molecules in Aqueous Solution," Applied Optics, vol. 34, No. 18, pp. 3208–3216, Jun. 20, 1995.

Peter M. Goodwin, W. Patrick Ambrose, and Richard A. Keller, "Single–Molecule Detection in Liquids by Laser–Induced Fluorescence," Accounts of Chemical Research, vol. 29, No. 12, pp. 607–613, 1996.

C. Zander, M. Sauer, K. H. Drexhage, D. S. Ko, A. Schulz, J. Wolfrum, L. Brand, C. Eggeling, and C. A. M. Seidel, "Detection and Characterization of Single Molecules in Aqueous Solution," Applied Physics B, vol. 63, pp. 517–523, 1996.

M. Kollner, A. Fischer, J. Arden–Jacob, K. H. Drexhage, R. Muller, S. Seeger, and J. Wolfrum, "Fluorescence Pattern Recognition for Ultrasensitive Molecule Identification: Comparison of Experimental Data and Theoretical Approximations," Chemical Physics Letters, vol. 250, pp. 355–360, 1996.

Jorg Enderlein, Peter M. Goodwin, Alan Van Orden, W. Patrick Ambrose, Rainer Erdmann, and Richard A. Keller, "A Maximum Likelihood Estimator to Distinguish Single Molecules by Their Fluorescence Decays," Chemical Physics Letters, vol. 270, pp. 464–470, 1997.

M. Sauer, C. Zander, R. Muller, B. Ullrich, K. H. Drexhage, S. Kaul, and J. Wolfrum, "Detection and Identification of Individual Antigen Molecules in Human Serum with Pulsed Semiconductor Lasers," Applied Physics B Lasers and Optics, vol. 65, Issue 3, pp. 427–431, 1997.

Alan Van Orden, Nicholas P. Machara, Peter M. Goodwin, and Richard A. Keller, "Single–Molecule Identification in Flowing Sample Streams by Fluorescence Burst Size and Intraburst Fluorescence Decay Rate," Analytical Chemistry, vol. 70, No. 7, pp. 1444–1451, Apr. 1, 1998.

C. Eggeling, J. R. Fries, L. Brand, R. Gunther, and C. A. M. Siedel, "Monitoring Conformational Dynamics of a Single Molecule by Selective Fluorescence Spectroscopy," National Academy of Sciences, vol. 95, pp. 1556–1561, 1998.

Markus Sauer, Jutta Arden–Jacob, Karl H. Drexhage, Florian Gobel, Ulrike Lieberwirth, Klaus Muhlegger, Ralph Muller, Jurgen Wolfrum, and Christoph Zander, "Time–Resolved Identification of Individual Mononucleotide Molecules in Aqueous Solution with Pulsed Semiconductor Lasers," Bioimaging, vol. 6, pp. 14–24, 1998.

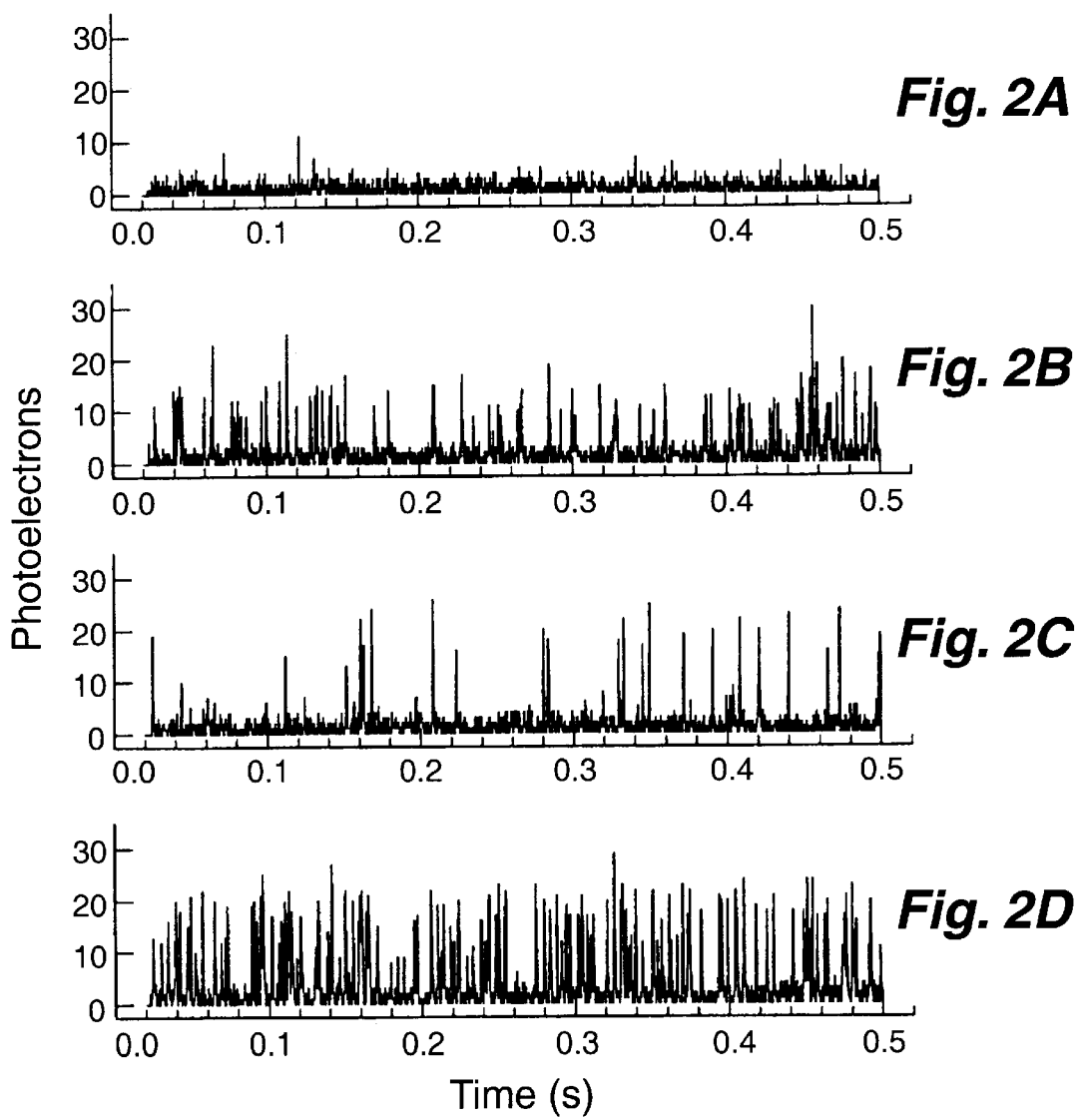

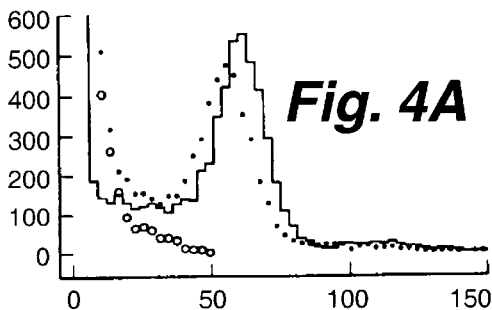
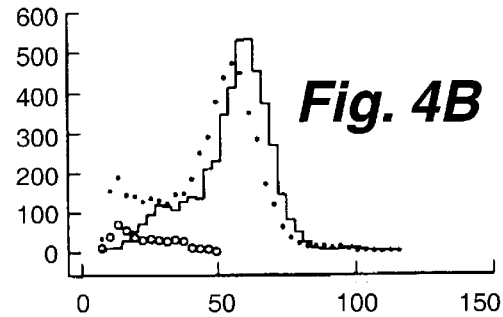
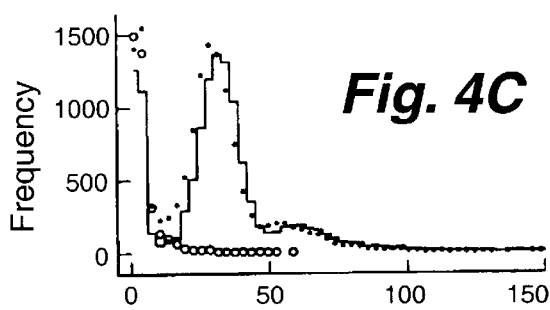
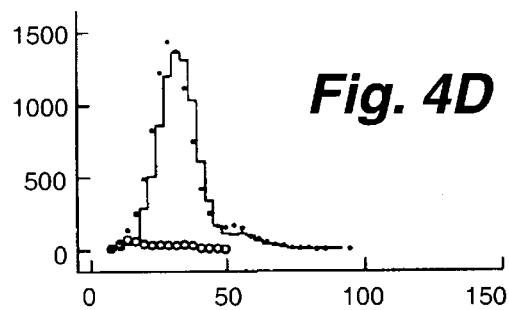
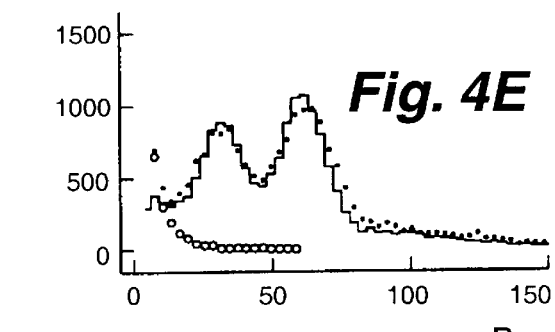
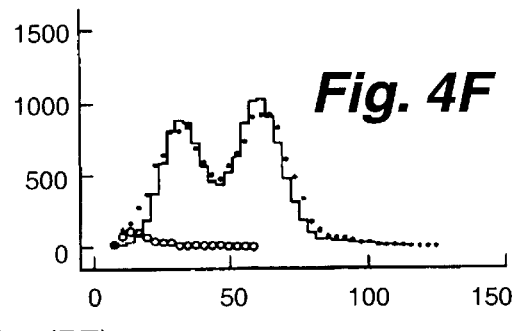

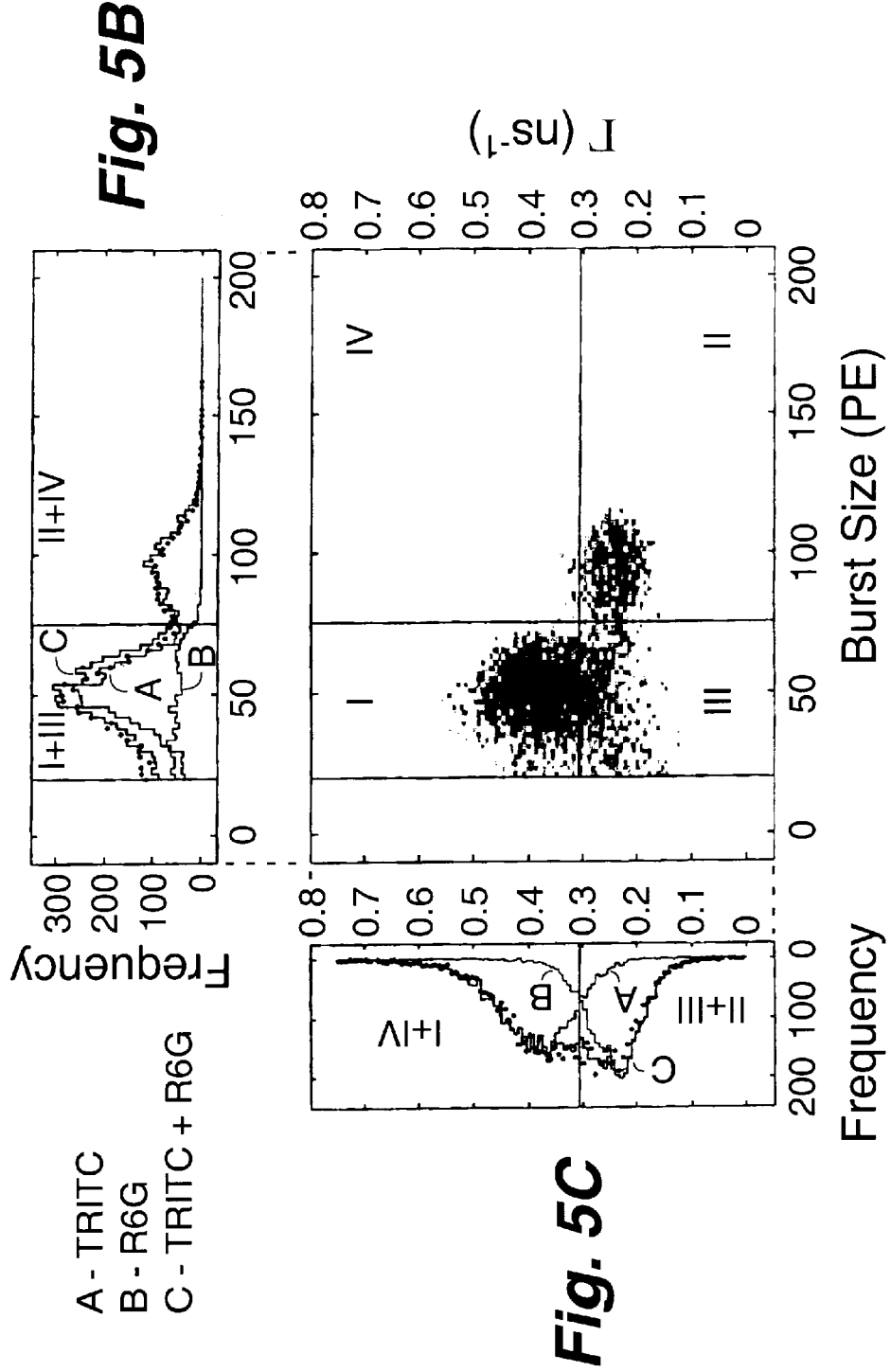

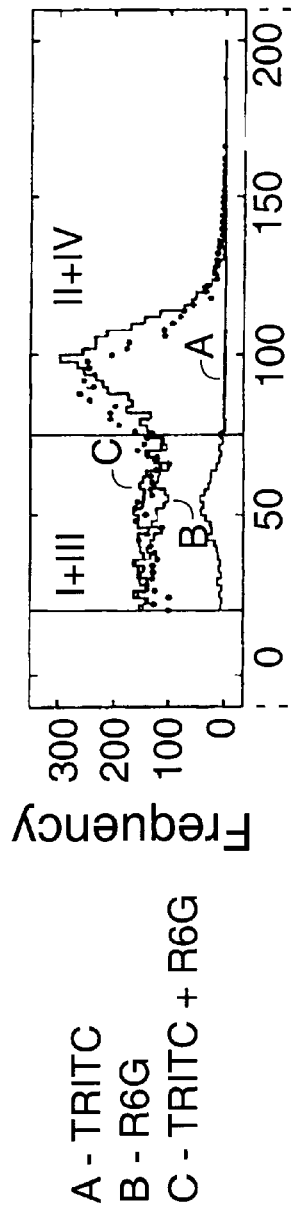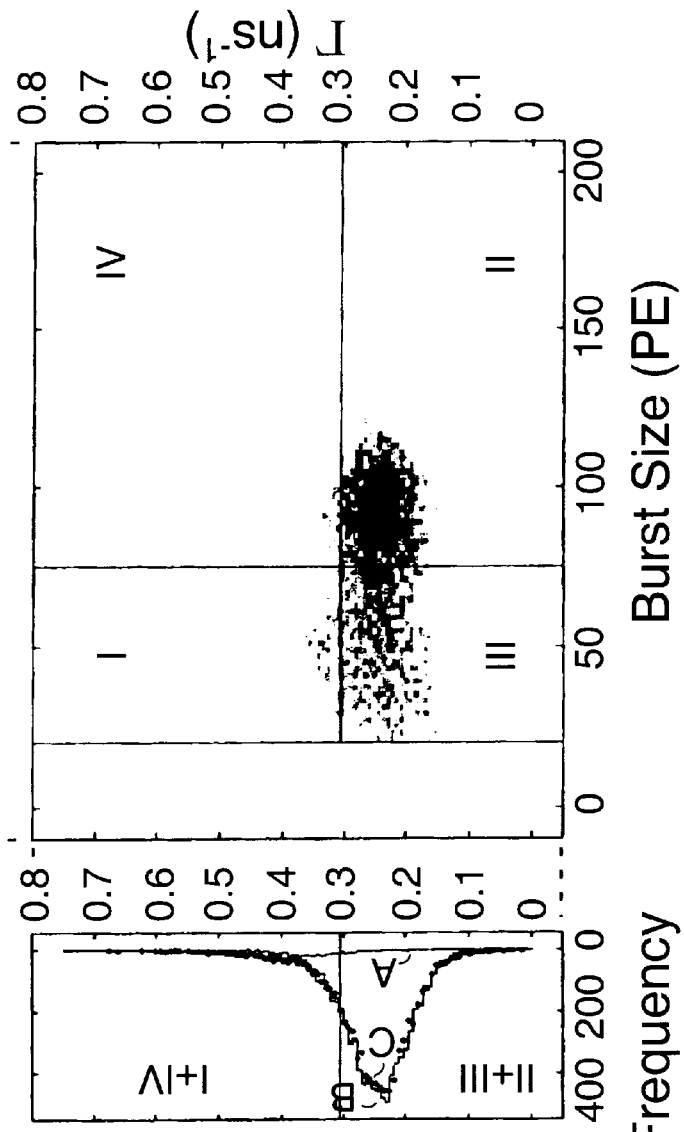
Fig. 5E
Fig. 5D
Fig. 5F
A - TRITC
B - R6G
C - TRITC + R6G

SINGLE MOLECULE IDENTIFICATION USING SELECTED FLUORESCENCE CHARACTERISTICS

RELATED CASES

This application claims the benefit of the priority date of provisional application Ser. No. 60/065,365, filed Nov. 12, 1997.

BACKGROUND OF THE INVENTION

This invention relates to flow cytometry and, more particularly, to applications of flow cytometry using single molecule identification. This invention was made with government support under Contract No. W-7405-ENG-36 awarded by the U.S. Department of Energy. The government has certain rights in the invention.

Light-induced fluorescence detection of single molecules in liquid solution was first accomplished several years ago, and applications for single molecule detection (SMD) in the analytical, environmental, and biomedical sciences are beginning to emerge. Overviews of single molecule detection in solution are presented in, e.g., R. A. Keller et al., 50 Appl. Spectrosc., pp. A12–A32 (1996), and P. M. Goodwin et al., 29 Accounts Chem. Res., pp. 607–613 (1996). In general, an operable system will include a dilute stream of separated individual molecules with known fluorescent characteristics that are excited one at a time by a light source, where the resulting emitted photons are detected. One approach to single molecule detection used herein is based on flow cytometry, where the analyte solution is delivered into a rapidly flowing sheath fluid and hydrodynamically focused into a narrow sample stream. Yet another approach is based on analyte movement through a capillary, such as described in U.S. Pat. No. 5,209,834, issued May 11, 1993, to Shera, and incorporated herein by reference.

In flow cytometry, a sample stream passes through the center of a probe volume defined by the diameter of the focused excitation laser beam and a spatial filter placed in the image plane of a light collecting objective. Single fluorescent molecules are detected by the bursts of photons emitted as they flow through the detection volume one-at-a-time. Hydrodynamic focusing of the sample stream by the sheath fluid ensures that the entire sample stream passes through the center of the excitation laser so that single molecules delivered into the flow cell are detected with an efficiency exceeding 90%. See, e.g., P. M. Goodwin et al., "Progress toward DNA sequencing at the single molecule level," 41 Exp. Tech. Phys., pp. 279–294 (1995), incorporated herein by reference.

Some of the applications under development for efficient single molecule detection in flow include DNA fragment sizing, DNA sequencing, counting and sorting of single molecules, and detection of probe-target binding. A number of applications for SMD in solution require one to distinguish between different fluorophores present in a mixture. For example, in one approach to DNA sequencing (U.S. Pat. No. 4,962,037, issued Oct. 9, 1990, and incorporated herein by reference), each base is labeled with a different fluorescent probe, and a rapid, efficient method is needed to identify these fluorophores. In yet another approach, only two fluorescent probes are required (U.S. Pat. No. 5,405,747, issued Apr. 11, 1995, and incorporated herein by reference) to reduce the number of distinguishing characteristics that are required to be identified.

Several techniques have been developed to distinguish between different single molecules in solution. One technique employs two or more detection channels to identify single molecules in a multicomponent mixture based upon differences in excitation and emission wavelengths of the fluorophore labels. See, e.g., Soper et al., "Detection and identification of single molecules in solution," 9 J. Opt. Soc. Am. B, pp.1761–1769 (October 1992), incorporated herein by reference. Typically, the detection volume is probed by collinear laser beams at different wavelengths corresponding to the excitation maxima of each of the fluorophores. A beam splitter directs the fluorescence from each fluorophore to a separate filter/detector channel. This method requires that the emission bands of the fluorophores be sufficiently separated to minimize crosstalk between the respective channels. Furthermore, separating the fluorescence signal into distinct detection channels increases the complexity of the instrumentation and can reduce the overall detection efficiency.

An alternative approach that requires only a single detection channel and is applicable to molecules with similar spectroscopic properties exploits the difference in fluorescence lifetimes of the fluorophores. Single Rhodamine 6G (R6G) molecules in flow have been distinguished from Rhodamine B (RB) molecules and from tetramethyl rhodamine isothiocyanate (TRITC) molecules by applying a maximum likelihood function to time-correlated single-photon counting (TCSPC) fluorescence decay measurements of individual bursts in a mixed sample (Zander et al.,63 Appl. Phys. B, pp. 517–523 (1996); J. Enderlein et al., 270 Chem. Phys. Lett., pp. 464–470 (1997)). Also, a rhodamine derivative JA169 has been distinguished from a carbocyanine dye Cy5 using this technique (M. Sauer et al., 65 Appl. Phys. B. No. 3, pp. 427–431 (August 1997).

Objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, this invention comprises a method for identifying single fluorescent molecules in a flowing sample stream. A sample stream is formed containing a dilute mixture of single molecule fluorophores, wherein each one of the fluorophores is serially ordered in the sample stream. The sample stream is illuminated with a single excitation wavelength laser beam effective to excite each fluorophore. Emitted photons from each said fluorophore are detected. In one embodiment, a burst size is determined for each fluorophore to identify each fluorophore. In another embodiment, the laser beam is formed of pulses, and a burst size and an intra-burst fluorescence decay rate ($\Gamma$) for each fluorophore are determined from fluorescence emission photons. The burst size and the decay rate are correlated to identify each fluorophore.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIGS. 2A–2D graphically depict single molecule fluorescence photon burst data from a photolysed ultrapure water blank, a dilute sample stream of TRITC, a dilute sample stream of R6G, and a dilute sample stream with a mixture of TRITC and R6G, respectively.

FIGS. 4A–4F graphically depict fluorescence photon burst size distributions (BSDs) compiled from data collected from a dilute sample stream of R6G, of TRITC and a mixture of R6G and TRITC (FIGS. 4A, 4C, 4E), and corresponding BSDs that are time filtered (FIGS. 4B, 4D, 4F).

FIGS. 5A and 5F are correlated single molecule burst size and intraburst fluorescence decay rate ($\Gamma$) measurements for a sample stream containing approximately equal amounts of TRITC and R6G (FIGS. 5A–C) and a sample stream containing mostly R6G (FIGS. 5D–F).

DETAILED DESCRIPTION OF THE INVENTION

In accordance with the present invention, single molecule identification (SMI) is based on differences in detected fluorescence burst intensities from fluorescent molecules. These intensity differences are a consequence of the different photophysical properties (absorption cross-sections, fluorescence quantum yields, and fluorescence emission spectra) of different fluorescent molecules. Unlike discrimination methods based on separate excitation wavelengths and emission detection channels or by fluorescence decay rates, burst intensity discrimination requires that the molecules experience a similar excitation irradiance during their transit across an excitation laser beam. The excitation laser beam may be either a pulsed laser beam or a continuous-wave laser beam. To accomplish this, the molecules are constrained to a sample stream diameter within the focused excitation laser. As with fluorescence decay rate measurements, this technique can be applied to molecules with similar spectroscopic properties and requires only a single excitation wavelength and fluorescence emission detection channel. In addition, a multiplex technique, wherein individual fluorescent molecules are distinguished by simultaneous measurement of fluorescence burst intensity and intra-burst fluorescence decay rate, provides a relatively high probability of individual fluorescent molecule identification. When intra-burst fluorescence decay rate is determined, the excitation laser beam must be a pulsed laser beam.

EXPERIMENTAL SECTION

Single molecule detection (SMD) in a flowing sample stream has been detailed in several publications, as noted in the Background of the Invention. The experimental techniques and results presented herein are also reported in Van Orden et al., "Single-Molecule Identification in Flowing Sample Streams by Fluorescence Burst Size and Intraburst Fluorescence Decay Rate," 70 *Anal. Chem. No.* 7, pp. 1444–1451 (Apr. 1, 1998), incorporated herein by reference. An operable system requires only a sample stream having an ordered flow of molecules that pass through the center of an excitation and detection volume. The experimental apparatus described herein provides increased efficiency for the detection of single molecules and is a preferred apparatus, but the present invention is not limited to flow cytometry. Other devices are available that provide an ordered stream of molecules, e.g., capillary flow and microchannels, and are known to persons of ordinary skill in the detection of single molecules and are within the scope of the present invention.

Figure 1:
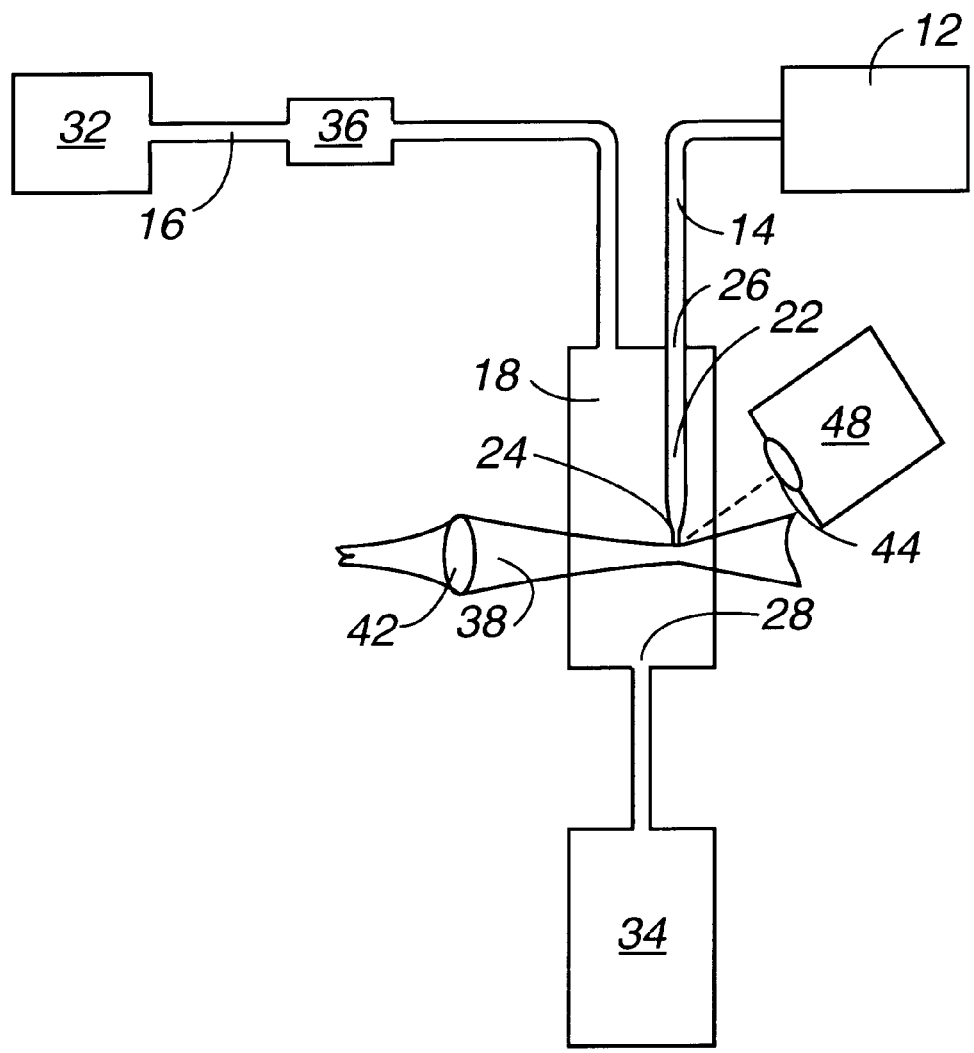
FIG. 1 schematically depicts apparatus for identifying single fluorescent molecules.

To obtain the results reported below, apparatus similar to that schematically shown in FIG. 1 was used. The parameters specified below are exemplary only and not intended to limit the scope of the present invention. Solutions 12 of, e.g., R6G and TRITC fluorophore molecules dissolved in ultrapure water, were delivered 14 into a sheath fluid 16, flowing through a square bore flow cell 18 (250×250 $\mu m^2$), from fused silica capillary 22 (10 $\mu$m i.d., 140 $\mu$m o.d.). The outlet tip 24 of the capillary was etched to a narrow taper using hydrofluoric acid to facilitate smooth laminar flow of the sheath fluid around the capillary. The inlet end 26 of sample introduction capillary 22 was positioned ~20 cm above outlet 28. A vacuum regulator (not shown) was used to apply a partial vacuum on the inlet end of the capillary to control the sample introduction rate. This configuration resulted in a sample stream diameter of approximately 10 $\mu$m. Sheath fluid 16 was ultrapure water delivered to the top of flow cell 18 by pump 32, which is a syringe pump in the experimental embodiment, but could be any controllable fluid delivery system, such as gravity feed, a positive displacement pump, or a roller-type pump. A second pump 34, which was also a syringe pump in the experimental embodiment, was used to move sheath fluid 16 through flow cell 18 at a volumetric flow rate of nominally 25–50 $\mu\lambda.min^{-1}$.

Fluorescent impurities present in sheath fluid 16 were photolyzed by passing the sheath fluid through a ~1 m-long photolysis cell 36 before it entered the flow cell, as described in U.S. Pat. application Ser. No. 08/727,841, incorporated herein by reference. Fluorescence was induced by irradiating the sample stream ~25 $\mu$m downstream from the capillary tip with a 514.5 nm mode-locked argon ion laser beam 38 (82 MHz repetition rate, 200 ps pulse width, 20–30 mW average power) focused to a circular spot of 16 $\mu$m ($e^{-2}$) diameter by a 75 mm focal length lens 42. A 60×, 1.2 NA water immersion microscope objective 44 was used to collect emitted fluorescence photons along an axis orthogonal to the flow and excitation axes. A 600 $\mu$m-wide, 1000 $\mu$m-high slit (not shown), with the long axis oriented parallel to the flow axis, was placed in the image plane of the collection objective to limit the size of the detection volume to ~2 p $\pi$. Emitted fluorescence photons were converted to photoelectrons by conventional detection electronics 48 and recorded as photon detection events.

Hydrodynamic focusing of the sample stream by the sheath fluid to a diameter of ~10 $\mu$m ensured that the entire sample stream flowed through the central portion of the detection volume. When this is the case, SMD efficiencies >90%, essentially limited by the photostability of the fluorescent species, are possible. Light passing through the slit was spectrally filtered with a bandpass filter (575±15 nm) (not shown) and focused onto a single photon counting avalanche photodiode within detection electronics 48 using a 32×microscope objective. Time-correlated single photon counting (TCSPC) was used to measure the elapsed time between the excitation laser pulse and each detected photon. Background due to Raman and Rayleigh scattering of the excitation laser beam by the solvent was suppressed by rejecting photon counts detected within ~1 ns of the laser pulse.

DATA ANALYSIS

Each detected photon arriving with a delay >1 ns with respect to the excitation laser pulse (gated photon) was recorded. The record consists of detection times (with respect to the previous gated photon) for each gated photon as well as the arrival time of the photon with respect to the excitation laser pulse. A photon burst is evidenced by a series of successive gated photons recorded at a high rate (40–100 kHz) compared to the background counting rate (~5 kHz). Details of the TCSPC apparatus and the algorithm used to search data sets for photon bursts are described in, e.g., P. M. Goodwin et al., 1895 *P. Soc. Photo-opt Ins.,* pp. 79–89 (1993), incorporated herein by reference.

Here, burst search threshold times of 75 and 50 $\mu$s were used for data collected with 20 and 30 mW of average excitation laser power, respectively. Successive gated photons (photoelectrons) detected at time intervals less than the threshold time comprise a photon burst. Each detected photon burst is characterized by three parameters: (1) the number of photoelectrons (PE) comprising the burst (burst size); (2) the duration of the burst (accumulated time below threshold); and (3) the intra-burst fluorescence decay rate ($\Gamma$). The intra-burst fluorescence decay rate is the reciprocal of the fluorescence lifetime $\tau_f$, where $\Gamma = 1/\lambda_f$. While the decay rate is the preferred parameter for the present invention, it is intended herein that the use of fluorescence decay rates include the use of fluorescence lifetimes, if desired by an experimenter. The intra-burst fluorescence decay rate was estimated from the distribution of intra-burst photon arrival times measured with respect to the excitation laser pulse, using a maximum likelihood estimator for a background free, single exponential decay (J. Tellinghuisen et al., "Analysis of Fluorescence Lifetime Data for Single Rhodamine Molecules in Flowing Sample Streams," 66 *Anal. Chem.,* pp. 64–72 (1994), incorporated herein by reference). To reduce contributions due to background bursts and accidental coincidences (a fluorescence burst recorded with two or more analyte molecules in the detection volume simultaneously), bursts were time-filtered, that is, bursts with durations significantly shorter or longer (see below) than the mean molecular transit time across the detection volume were discarded.

The following procedure was used to estimate the probabilities for misidentification of the two fluorophores and to characterize the most probable sources of error. A Monte Carlo (MC) simulation was used to generate fluorescence burst data from a simulated flow cytometry-based SMD experiment, given the photophysical properties of the analyte molecules (absorption cross section, fluorescence quantum yield, fluorescence lifetime, photodestruction quantum yield, optical saturation intensity), analyte fluorescence emission detection efficiencies of the apparatus, excitation laser parameters (pulse repetition rate, average power, focused spot size), and flow parameters (analyte concentration, sample stream flow velocity). The simulation accounts for spatial variations of the excitation laser intensity and fluorescence collection efficiency within the detection volume, as well as diffusion, photobleaching, and optical saturation of the analyte molecules during their transit through the detection volume. Good agreement between the simulation and the experimental data was achieved by making slight adjustments to the estimated optical collection/detection efficiency of the apparatus. For the R6G simulation, it was also necessary to adjust the photodestruction efficiency, as further discussed in Van Orden et al.,supra.

P. M. Goodwin, et al., 1895 P. Soc. Photo-op Ins., supra., describes the application of a Monte Carlo simulation to model the fluorescence burst size distribution detected from single Rhodamine-110 molecules excited in flow. The simulation has been modified to model the TCSPC data of the simulated bursts as well as the fluorescence burst sizes. For each detected photon, a random deviate drawn from the appropriate TCSPC arrival time distribution (R6G, TRITC, or background fluorescence) was used to assign a time separation between that detected photon and the excitation laser pulse. The background photon arrival time distribution was compiled directly from the experimental data by excluding photons detected inside of photon bursts. R6G and TRITC fluorescence photon arrival time distributions were constructed by multiplication of single exponential decays (4.0 and 2.3 ns for R6G and TRITC, respectively, taken from bulk TCSPC measurements of these dyes) by the TCSPC photon arrival distribution measured from an uncorrelated light source (ideally, a flat distribution) to account for nonlinearities of the TCSPC system.

RESULTS AND DISCUSSION

For all data sets presented in FIGS. 2A–D, 3A–B, and 4A–F, the average excitation laser power was 20 mW. The sheath fluid volumetric flow rate was 40 $\mu\lambda$ min$^{-1}$; the e$^{-2}$ transit time across the detection volume, derived from the autocorrelation function of the photon burst data, was 1.2 ms; and the velocity of the sample stream through the detection volume, estimated from the MC simulation, was 1.2 cm/sec.

FIGS. 2A–D display 500 ms of raw fluorescence burst data binned at 250 $\mu$s intervals from a photolyzed ultrapure water blank (FIG. 2A) and dilute sample streams of TRITC (FIG. 2B), R6G (FIG. 2C), and a mixture of R6G and TRITC (FIG. 2D). A comparison of FIGS. 2B and 2C clearly shows that the fluorescence burst sizes detected for single TRITC molecules are, on average, smaller than those detected for R6G As discussed above, the fluorescence burst size of a single fluorophore is determined by such photophysical properties as the absorption cross section at the excitation wavelength, the fluorescence quantum yield, the fluorescence lifetime, the overlap of the fluorescence emissions, and the spectral bandwidth of the detection channel. For TRITC, the peak in the absorption spectrum occurs near 554 nm. Therefore, excitation at 514.5 nm does not occur as efficiently as for R6G, with an absorption maximum at 528 nm. Furthermore, the fluorescence quantum yield of R6G (0.9) is almost three times that of TRITC (0.35). To improve the relative fluorescence emission detection efficiency for TRITC, a spectral bandpass filter was used in the detection channel that favored the fluorescence emission maximum of TRITC.

Figure 3A:
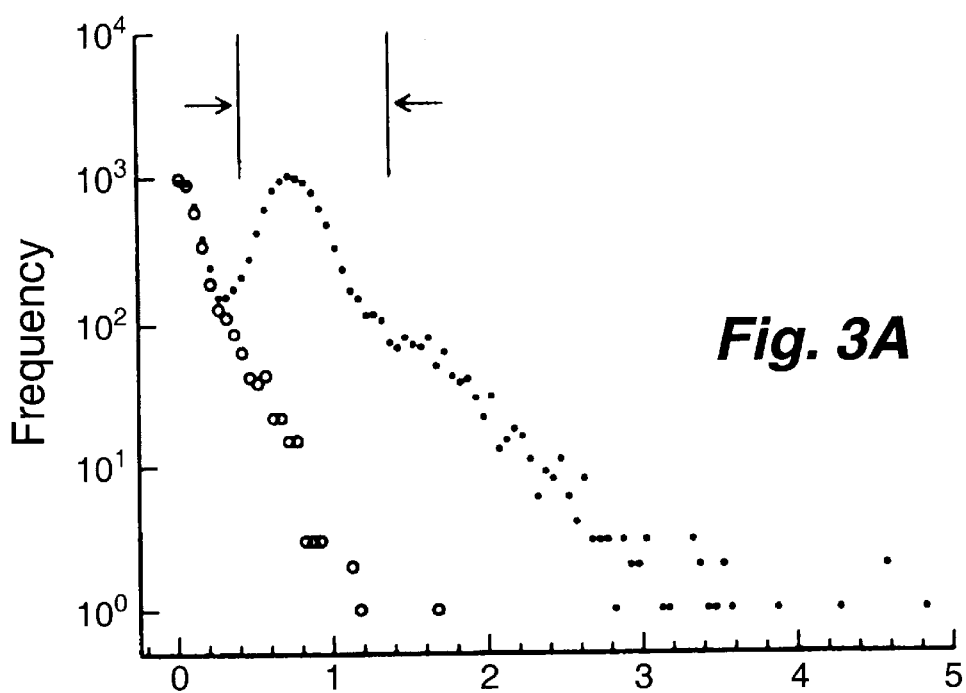
FIGS. 3A and 3B graphically depict single molecule fluorescence burst duration distributions measured from dilute sample streams of TRITC and R6G, respectively.
Figure 3B:
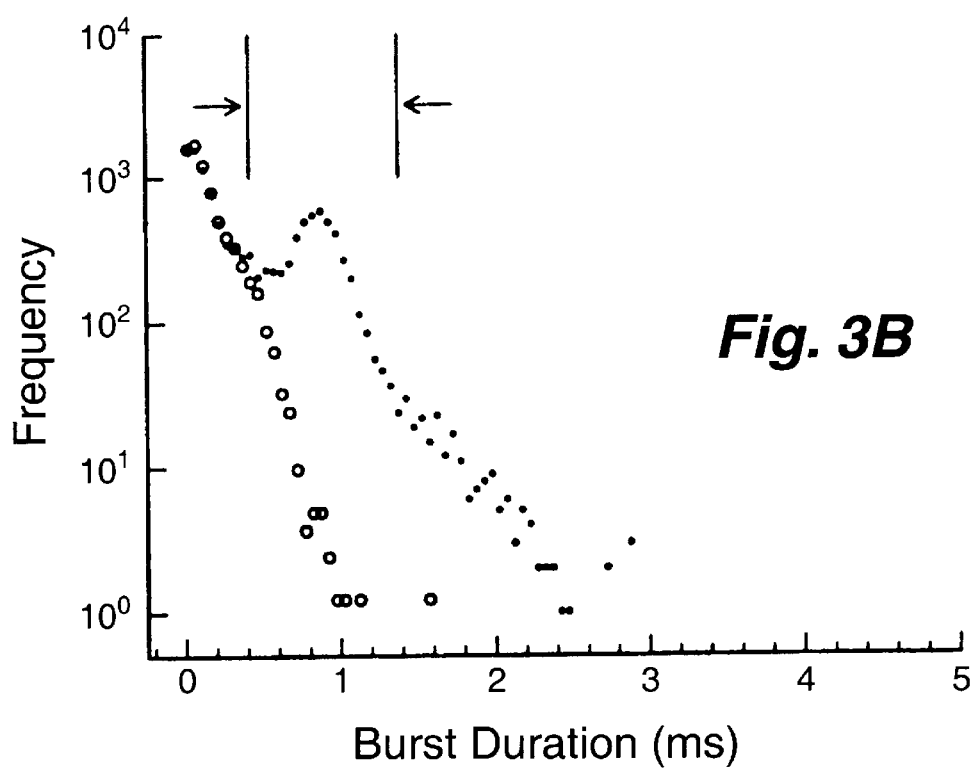

FIGS. 3A and 3B display fluorescence burst duration distributions (BDD) compiled from data collected from dilute sample streams of TRITC (FIG. 3A) and R6G (FIG. 3B). Experimental conditions were the same as for the data shown in FIGS. 2A–D. BDDs compiled from data collected with the sample stream ON are shown with solid circles; BDDs collected with the sample stream OFF and misaligned with respect to the detection volume are shown with open circles. The peak in each distribution gives the mean detected burst duration for unphotobleached TRITC and R6G molecules under these experimental conditions. Note that the mean detected burst durations are significantly shorter than the e$^{-2}$ transit time (1.2 ms) derived from the autocorrelation function. This is a consequence of the burst search algorithm threshold. The majority of single molecule fluorescence bursts fall in a time range (0.42–1.38 ms) denoted by the vertical lines and arrows in FIGS. 3A and 3B. Shorter bursts are primarily due to photoelectrons associated with Raman scattering that "leak" through the time gates, and longer bursts are mostly accidental coincidences. Thus, a time-filter can be selected to discriminate against background emissions and accidental coincidence bursts in the data in real-time during data collection or, as is done here, in a post-processing step.

FIGS. 4A–F display size distributions of emitted fluorescence photon bursts compiled from data collected under the same conditions as for FIGS. 2A–D and 3A–B. Burst size distributions (BSD) shown with closed circles in FIGS. 4A, 4C, and 4E were compiled from data collected from dilute sample streams of R6G, TRITC, and a R6G/TRITC mixture, respectively. Open circles are BSDs compiled from the water blank (data collected with the sample stream OFF and misaligned with respect to the detection volume).

FIGS. 4B, 4D, and 4F, display BSDs that were obtained after the burst data was time-filtered to remove bursts less than 0.42 ms and greater than 1.38 ms in duration. This time-filtering procedure was done to reduce the number of background bursts (<0.42 ms) and bursts resulting from two or more molecules simultaneously present (>1.38 ms) in the detection volume from the data set. Note the marked reduction in the number of smaller (<20 PE) bursts primarily due to background emissions. It must be emphasized that the background BSDs were not subtracted from the analyte BSDs to obtain the time-filtered distributions shown in FIGS. 4B, 4D, and 4F.

The peaks in the BSDs at ~30 and ~60 PE correspond to the average fluorescence burst sizes detected from single TRITC and R6G molecules, respectively, that did not photobleach while crossing the detection volume. The fact that peaks are observed in the BSDs indicates that the diameter of the sample stream was indeed smaller than the detection volume and was well aligned to the laser beam. Were this not the case, the BSD would simply decrease monotonically away from zero PE, i.e., the BSD is a maximum at 0 PE.

FIGS. 4E and 4F show raw and time-filtered BSDs obtained from the mixture of TRITC and R6G. Two well-resolved peaks at 30 and 60 PE are observed, corresponding to different BSDs for TRITC and R6G, respectively. This result confirms that these fluorophores can be distinguished at the single molecule level based on their different fluorescence burst sizes. The solid curves in FIGS. 4A–4F are BSDs obtained from synthetic data generated by the MC simulation described above. The simulation parameters were adjusted to give the best fits to the mixture in FIGS. 4E and 4F. These same parameters were then used for the simulations of the pure R6G and TRITC solutions.

Table 1 presents the parameters used in the simulation. Asterisks indicate parameters that were adjusted to achieve the best fit. A time-filtered burst size detection threshold of 14 PE was chosen as a good compromise between background burst rate and SMD efficiency. Time-filtered bursts smaller than 14 PE in size are not counted as single molecule fluorescence bursts. For this threshold, the simulation indicates that 96% of the TRITC molecules and 78% of the R6G molecules that are introduced into the sheath flow are detected by apparatus used herein. The smaller efficiency obtained for R6G was due to the larger photodestruction quantum yield for this molecule.

TABLE 1

Monte Carlo Simulation Parameters

| Parameter | R6G | TRITC |
|---|---|---|
| Absorption cross section $\sigma_{514nm}$ ($10^{-16}$ cm$^2$) | 2.2 | 1.6 |
| Fluorescence quantum yield | 0.9 | 0.35 |
| Fluorescence lifetime (ns) | 4.0 | 2.3 |
| Photodestruction quantum yield ($10^{-6}$) | 80* | 6 |
| Saturation intensity ($10^5$ W cm$^{-2}$ s$^{-1}$) | 0.55 | 1.14 |
| Diffusion constant ($10^{-8}$ cm$^2$ s$^{-1}$) | 300 | 300 |
| Bandpass filter fluorescence emission transmission | 0.16 | 0.27 |
| Time-gate fluorescence emission transmission | 0.84 | 0.74 |
| Excitation laser $\theta^{-2}$ beam diameter ($10^{-4}$ cm) | 16 | 16 |
| Averge excitation laser power ($10^{-3}$ W) | 20$^+$, 30$^{++}$ | 20$^+$, 30$^{++}$ |
| Sample flow velocity (cm s$^{-1}$) | 1.23$^+$, 0.9$^{++}$ | 1.23$^+$, 0.9$^{++}$ |
| Overall optical collection/detection efficiency excluding bandpass filter and time gate transmissions | 0.093**, 0.085*** | 0.093**, 0.085*** |
| Detection electronics dead time ($10^{-6}$) | 4 | 4 |

*values adjusted to fit experimental data
$^+$For data in FIGS. 2–4; $^{++}$For data in FIG. 5

In order to fit the R6G burst size distribution (FIG. 3A), the photodestruction quantum efficiency of R6G was adjusted to a final value of $8\times10^{-5}$. This value is larger than the value of $2\times10^{-5}$ reported in the literature. In FIG. 4B, a shoulder is observed toward the low photoelectron side of the peak. This shoulder is due to R6G molecules that photobleached during their transit through the detection volume. A much smaller shoulder is seen for the TRITC peak in FIG. 4D due to the higher photostability of TRITC. The simulation herein indicates that 44% of the detected R6G molecules photobleach while crossing the detection volume compared to 4% of the TRITC molecules.

A single molecule identification (SMI) threshold of 45 PE was chosen; bursts greater than or equal to this threshold are identified as R6G single molecule fluorescence bursts and bursts <45 PE are identified as TRITC bursts. According to the MC simulation, 75% of detected R6G single molecule bursts are $\geq$45 PE in size, and 25% are detected below this threshold. Of the detected TRITC single molecule bursts, 96% are <45 PE in size and 4% give bursts $\geq$45 PE; 97% of the unphotobleached R6G molecules are detected with bursts $\geq$45 PE. Clearly, photodestruction of R6G molecules as they transit the detection volume increases error rates for SMI based on fluorescence burst size alone. But, as indicated by FIGS. 4E and 4F, increasing the photostability of the brighter component will reduce the overlap of the burst size distributions and decrease the SMI error rates.

To improve the accuracy of SMI, simultaneous, correlated measurements of the burst size and intra-burst fluorescence decay rate were performed for each detected burst in R6G/TRITC mixtures. For these measurements, the flow velocity of the sample stream through the detection volume was lowered to 0.9 cm s$^{-1}$ and the average excitation power was raised to 30 mW to increase the average number of PE detected per burst.

FIGS. 5A and 5B show correlated burst size (PE) and fluorescence decay rate ($\Gamma$) measurements from dilute sample streams containing approximately equal amounts of TRITC and R6G (FIG. 5A) and containing mainly R6G (FIG. 5B). Analyte molecule introduction rates estimated from MC simulations are 20 TRITC s$^{-1}$ and ~20 R6G s$^{-1}$ in FIG. 5A; and ~65 R6G s$^{-1}$ and ~3 TRITC s$^{-1}$ in FIG. 5B. The correlated data are displayed as two-dimensional histograms (scatter plots) with darker shades of grey indicating increasing numbers of events. Experimental conditions were: a sheath volumetric flow rate, 30 µλ min$^{-1}$; average excitation laser power, 30 mW; sample stream flow velocity, ~0.9 cm s$^{-1}$; and sample transit time (e$^{-2}$), ~1.8 ms. The burst data were time-filtered (0.25–2.0 ms) to reduce background bursts and accidental coincidences; only bursts ≧20 PE in size are shown. Again, no background subtraction was done to arrive at the distributions shown in the figures.

The PE-F plane was divided into four regions (I,II,III,IV) for SMI, as shown in FIGS. 5A and 5B. Projections of the correlated data onto the fluorescence decay rate and fluorescence burst size axes are shown to the left and above each scatter plot, respectively. Solid curves A and B plotted on the projections are estimates, based on MC simulations of the experiment, of TRITC and R6G contributions to the measured distributions, respectively. Curves C are sums of the estimated TRITC and R6G contributions. Vertical lines shown on the projections delimit regions that are used for distinguishing TRITC and R6G single molecule fluorescence bursts based on intra-burst fluorescence decay rate alone(TRITC≡I+IV, Γ≧0.307 ns$^{-1}$; R6G≡II+III, Γ<0.307 ns$^{-1}$) and burst size (TRITC≡I+III, 20≦PE<75; R6G≡II+IV, PE≧75).

Based on MC simulations for these experimental conditions and a time-filtered burst size detection threshold of ≧20 PE, the estimated SMD efficiencies are 97% for TRITC and 80% for R6G. Again, the lower detection efficiency for R6G is due to its high photodestruction quantum yield; approximately 66% of the R6G molecules photobleach while crossing the excitation laser, whereas only 7% of the TRITC molecules photobleach. The increased photobleaching rates (compared to FIGS. 4A–F) are due to the higher average excitation laser power (1.5×) and longer sample transit time (1.4×) used in this experiment.

According to the MC simulations, for SMI by burst size alone, 99% of the detected TRITC molecules give bursts ≧20 and <75 PE in size and fall into Region I+III; only 1% of the detected TRITC molecules give bursts >75 PE and fall into Region II+IV. 53% of the detected R6G molecules give bursts ≧75 PE and fall into Region II+IV, and 47% of the detected R6G molecules give bursts >20 and <75 PE in size and fall into Region I+III. Again, a large fraction of the detected R6G molecules are misidentified. This is a consequence of detected bursts from photobleached R6G molecules that fall into the size range (I+III) expected for TRITC bursts.

For SMI by intra-burst fluorescence decay rate (Γ) alone, 89% of the detected TRITC molecules give bursts with Γ≧0.307 ns$^{-1}$ and 11 % give bursts with Γ<0.307 ns$^{-1}$. For R6G, 88% of the detected molecules give bursts with Γ<0.307 ns$^{-1}$ and 12% give bursts with Γ≧0.307 ns$^{-1}$. Here the errors are a consequence of the overlap of the estimated fluorescence decay rate distributions for TRITC and R6G. The widths of these distributions are determined by the number of PE used to estimate the decay rate. Improvement of the overall photon collection/detection efficiency would result in more PEs detected per burst and narrower fluorescence decay rate distributions, thereby increasing the accuracy of SMI. Photobleaching does broaden the R6G distribution indirectly since, on average, fewer PEs are used to estimate fluorescence decay rate of photobleached R6G molecules. However, this effect is small compared to the direct effect that photobleaching has on the R6G burst size distribution.

For correlated, two-parameter SMI, two islands corresponding to fluorescence bursts detected from unphotobleached TRITC and R6G molecules are clearly visible in FIGS. 5A–C. TRITC bursts with a mean burst size of 53 PE and a mean intra-burst fluorescence decay rate of 0.38 ns$^{-1}$ cluster in Region I; unphotobleached R6G bursts with a mean burst size of 96 PE and a mean intra-burst fluorescence decay rate of 0.25 ns$^{-1}$ cluster in Region II. Region III contains mostly bursts from R6G molecules that photobleached while crossing the detection volume. This is clear from FIGS. 5D–F where the sample consisted mainly of R6G. Photobleached R6G molecule fluorescence bursts comprise a "tail" on the unphotobleached R6G distribution that extends from Region II across Region III.

Based on the MC simulation, probabilities are assigned for detected TRITC and R6G bursts to fall into Regions I–IV. These are tabulated in Table 2.

TABLE 2

Single Molecule Identification Probabilities

|  | I | II | III | IV |
|---|---|---|---|---|
| TRITC | 0.883 | 0.001 | 0.108 | 0.008 |
| R6G | 0.078 | 0.489 | 0.390 | 0.044 |

Probabilities for detection in regions delineated for SMI by burst size (I+III,II+IV) and intra-burst fluorescence decay rate (I+IV,II+III) alone were obtained by summing the appropriate entries in Table 2. These calculations ignore accidental coincidences and are strictly valid only for SMD rates small compared to the reciprocal of the molecular transit time across the detection volume.

It is interesting to calculate the confidence level for identification as R6G or TRITC for events that occur in the specific regions. This level depends on the relative detection rates of the two molecules. For example, for SMI by burst size alone, the magnitude of the tail of the TRITC BSD extending into Region II+IV depends on the detection rate of TRITC. Likewise the magnitude of the shoulder of the R6G BSD into Region I+III depends on the detection rate of R6G.

The fraction of bursts falling into a given region due to TRITC or R6G can be calculated from the relative detection rates for these species and the SMI probabilities given in Table 2. Table 3 is a tabulation of the fraction of bursts detected in a region due to a specific fluorophore for three different sample stream concentration ratios of TRITC and R6G ([TRITC]/[R6G]=0.25, 1, 4). For example, comparison of the results for an equimolar sample shows that the highest SMI confidences are obtained for the correlated measurement in Regions I (93% of the bursts detected in this region are due to TRITC) and II (99.8% for R6G). SMI by burst size alone gives only a 72% confidence for TRITC (Region I+III) and a 98% confidence for R6G (Region II+IV). SMI by intra-burst fluorescence decay rate alone gives a 90% identification confidence for TRITC (Region I+IV) and a 87% confidence for R6G (Region II+III).

TABLE 3

Single Molecule Identification Confidence Levels

| | 1 Parameter - Burst Size | | |
|---|---|---|---|
| TRITC\|R6G | | I + III | II + IV |
| 0.25 | TRITC | 0.39 | 0.006 |
|  | R6G | 0.61 | 0.994 |
| 1.0 | TRITC | 0.72 | 0.02 |
|  | R6G | 0.28 | 0.98 |

TABLE 3-continued

Single Molecule Identification Confidence Levels

| | | | |
|---|---|---|---|
| 4.0 | TRITC | 0.91 | 0.08 |
| | R6G | 0.09 | 0.92 |

1 Parameter: Fluorescence Decay Rate

| TRITC\|R6G | | I + IV | II + III |
|---|---|---|---|
| 0.25 | TRITC | 0.69 | 0.04 |
| | R6G | 0.31 | 0.96 |
| 1.0 | TRITC | 0.90 | 0.13 |
| | R6G | 0.10 | 0.87 |
| 4.0 | TRITC | 0.97 | 0.38 |
| | R6G | 0.03 | 0.62 |

2 Parameter: Burst Size + Fluorescence Decay Rate

| TRITC\|R6G | | I | II | III | IV |
|---|---|---|---|---|---|
| 0.25 | TRITC | 0.77 | 0.001 | 0.08 | 0.05 |
| | R6G | 0.23 | 0.999 | 0.92 | 0.95 |
| 1.0 | TRITC | 0.93 | 0.002 | 0.25 | 0.18 |
| | R6G | 0.07 | 0.998 | 0.75 | 0.82 |
| 4.0 | TRITC | 0.98 | 0.01 | 0.57 | 0.47 |
| | R6G | 0.02 | 0.99 | 0.43 | 0.53 |

CONCLUSIONS

Thus, in accordance with the present invention, single molecules in mixed sample streams may be distinguished with high accuracy based on differences in fluorescence burst intensity or a combination of fluorescence burst intensity and intra-burst fluorescence decay rate, both using only a single excitation wavelength and a single fluorescence emission detection channel. For the analytes studied here, TRITC and R6G, SMI confidence levels for TRITC are limited mainly by the photostability of R6G. Increasing the photostability of the analytes by, for example, the addition of an anti-fade reagent is expected to result in significant improvement of SMI confidence levels.

An immediate application is to single molecule DNA sequencing. Sequencing multiple identical DNA strands individually and combining the results to form a consensus sequence will reduce error rates below those reported here. For example, given a random error for sequencing an individual DNA strand of 20% per base, the calculations show that the error for a consensus sequence having only 10 DNA strands is reduced to less than 1%.

While the above examples are based on the pair of dyes Rhodamine 6G and TRITC, many other dye selections can be identified readily by a person skilled in the art of fluorescence detection. Since only one excitation wavelength and a single detection channel are used, the various fluorescent species chosen for SMI must have overlapping excitation and overlapping emission spectra. The excitation wavelength and emission bandpass filter wavelength must be chosen such that the fluorescent species can both be detected at the single molecule level with photon bursts of sufficient size (greater than about 25 detected photons per burst) for intra-burst fluorescence decay measurements to be obtained.

In the absence of optical saturation and photobleaching, the intensity of photon bursts from a given species scales as the product of the absorption cross-section and the fluorescence quantum yield of the molecule. Photobleaching will reduce the average burst size and broaden the burst size distribution. Both the excitation wavelength and detection channel bandpass filter center position and width can be adjusted to optimize differences between the average detected photon burst intensities of the different fluorescent species.

The fluorescence decay rate of a given species is determined by its photophysical properties and interactions between it and its immediate environment (e.g., the solvent). The chosen species must have fluorescence decay rates sufficiently different such that they can be discriminated at the single molecule (photon burst) level. Given the current state of the art for overall photon collection/detection efficiencies (1%–5%), the decay rate ratio of the chosen species should be at least 1.5 for SMI based on lifetime alone. This ratio is expected to decrease as detection technology improves. Differences in the species' average photon burst intensities allows SMI with smaller decay rate ratios (closer to unity).

In general, for single molecule identification by fluorescence burst size or by a combination of fluorescent burst size and intra-burst fluorescence decay rate, a condition is selected to maximize the resolution between the species in the burst size and burst size/fluorescence decay rate plane. SMD efficiencies and SMI error rates for a given pair of dyes can be predicted using a MC simulation that incorporates photophysical constants of the dyes and selected experimental parameters. Some possible fluorescent dye pairs for SMI according to the above criteria are provided in Table 4.

TABLE 4

Dye Combinations for SMI

| Dye 1 | abs/em (nm) | $\Gamma$ (ns)$^{-1}$ | Dye 2 | abs/em (nm) | $\Gamma$ (ns)$^{-1}$ |
|---|---|---|---|---|---|
| Lisamine Rhodamine B | 570/590 | 0.475 | Texas Red | 595/615 | 0.250 |
| Rhodamine B | 570/590 | 0.556 | Oregon Green 514 | 511/530 | 0.238 |
| TRITC | 555/580 | 0.475 | BODIPY Fl | 505/513 | 0.175 |
| R6G | 528/555 | 0.263 | TRITC | 555/580 | 0.475 |
| Cresyl Violet Perchlorate | 610/620 | 0.313 | BODIPY TR | 589/617 | 0.185 |
| TRITC | 555/580 | 0.475 | Oregon Green 500 | 503/522 | 0.244 |
| Rhodamine B | 570/590 | 0.556 | Oregon Green 500 | 503/522 | 0.244 |
| TRITC | 555/580 | 0.475 | Rhodamine 101 Perchlorate | 570/590 | 0.231 |
| Rhodamine 700 | 652/678 | 0.475 | Rhodamine 800 | 682/716 | 0.91 |
| Cresyl Violet Perchlorate | 610/620 | 0.313 | Rhodamine B | 570/590 | 0.556 |
| Cy 5 | 655/675 | 0.665 | Cresyl Violet Perchlorate | 610/620 | 0.313 |

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for identifying single fluorescent molecules in a sample stream comprising the steps of:

forming a sample stream containing a dilute mixture of selected single molecule fluorophores, wherein each one of said fluorophores is serially ordered in said sample stream;

passing said serially ordered fluorophores one at a time through a detection volume;

illuminating said sample stream within said detection volume with a pulsed laser beam at a single excitation wavelength effective to excite said fluorophores;

detecting emitted photons from each one of said fluorophores to output corresponding photon detection events;

determining from said photon detection events a photon burst size and an intra-burst fluorescence decay rate for each one of said fluorophores; and correlating said burst size and said decay rate with known characteristics for each one of said fluorophores to identify each one of said fluorophores.

2. A method according to claim 1, wherein said sample stream has a diameter less than a diameter of said laser beam intercepting said sample stream.

3. A method according to claim 1, wherein the step of forming said sample stream includes the step of directing a sheath fluid about said sample stream to form a focused sample stream within said laser beam.

4. A method according to claim 1, further including the steps of:

photobleaching said sheath fluid; and introducing said dilute mixture of single molecule fluorophores within said sheath fluid after said photobleaching.

5. A method according to claim 1, further including the step of forming a photon record comprising a number of said photon detection events occurring within a time-gated window after a predetermined delay with respect to an exciting pulse in said pulsed laser beam and a detection time for each one of said photon detection events that is relative to an immediately preceding photon detection event.

6. A method according to claim 1, wherein the step of determining said size of each said photon burst further includes the step of:

time filtering each said photon burst to output filtered burst data comprising a number of said photon detection events.

7. A method according to claim 1, wherein the step of determining said intra-burst fluorescence decay rate further includes the step of estimating said intra-burst fluorescence decay rate from arrival times of said photons measured with respect to said excitation laser pulses.

8. A method according to claim 1, wherein said fluorophores are selected to maximize the resolution between said fluorophores in burst size and fluorescence decay rate space.

9. A method for identifying single fluorescent molecules comprising the steps of:

forming a sample stream containing a dilute mixture of selected single molecule fluorophores, wherein each one of said fluorophores is serially ordered in said sample stream;

passing said serially ordered fluorophores one at a time through a detection volume;

illuminating said sample stream within said detection volume with a laser beam at a single excitation wavelength effective to excite said fluorophores;

detecting emitted photons from each said fluorophore to output corresponding photon detection events;

determining from said photon detection events a photon burst size for each one of said fluorophores; and correlating said burst size with known characteristics for each one of said fluorophores to identify each one of said fluorophores.

10. A method according to claim 9, wherein said sample stream has a diameter less than a diameter of said laser beam intercepting said sample stream.

11. A method according to claim 9, wherein the step of forming said sample stream includes the step of directing a sheath fluid about said sample stream to form a focused sample stream within said laser beam.

12. A method according to claim 9, further including the steps of:

photobleaching said sheath fluid; and introducing said dilute mixture of said single molecule fluorophores within said sheath fluid after said photobleaching.

13. A method according to claim 9, wherein the step of determining said size of said photon bursts further includes the step of:

time filtering each said photon burst to output filtered burst data comprising a number of said photon detection events.

14. A method according to claim 9, wherein said fluorophores are selected to maximize the resolution between said fluorophores in burst size space.

15. A method according to claim 9, wherein said laser beam is a pulsed laser beam.

16. A method according to claim 15, further including the step of forming a photon record comprising a number of said photon detection events occurring within a gated window after a predetermined delay with respect to an exciting pulse in said pulsed laser beam and a detection time for each one of said photon detection events that is relative to an immediately preceding photon detection event.

17. A method according to claim 16, wherein the step of determining said size of said photon bursts further includes the step of:

time filtering each said photon burst to output filtered burst data comprising a number of said photon detection events.

18. A method according to claim 16, wherein said fluorophores are selected to maximize the resolution between said fluorophores in burst size space.

* * * * *